(12) United States Patent
Mogensen et al.

(10) Patent No.: US 7,654,484 B2
(45) Date of Patent: Feb. 2, 2010

(54) APPARATUS FOR AND A METHOD OF ADJUSTING THE LENGTH OF AN INFUSION TUBE

(75) Inventors: Lasse Wesseltoft Mogensen, Søborg (DK); Magnus Walter Göransson, Göteborg (SE)

(73) Assignee: Unomedical A/S, Birkeroed (DK)

( * ) Notice: Subject to any disclaimer, the term of this patent is extended or adjusted under 35 U.S.C. 154(b) by 444 days.

(21) Appl. No.: 10/526,253

(22) PCT Filed: Sep. 2, 2003

(86) PCT No.: PCT/DK03/00571

§ 371 (c)(1),
(2), (4) Date: Feb. 8, 2006

(87) PCT Pub. No.: WO2004/020036

PCT Pub. Date: Mar. 11, 2004

(65) Prior Publication Data

US 2006/0186256 A1   Aug. 24, 2006

Related U.S. Application Data

(63) Continuation-in-part of application No. 10/409,898, filed on Apr. 8, 2003, now abandoned.

(30) Foreign Application Priority Data

Sep. 2, 2002   (DK) ............................... 2002 01287

(51) Int. Cl.
*B65H 75/28* (2006.01)
*B65H 75/40* (2006.01)

(52) U.S. Cl. ................ 242/402; 242/405.1; 242/588.3; 242/610.6; 604/261

(58) Field of Classification Search ................. 242/388, 242/388.1, 402, 405, 405.1, 588, 588.3, 610, 242/610.6; 604/95.01, 95.02, 259, 261; 606/103; 600/585

See application file for complete search history.

(56) References Cited

U.S. PATENT DOCUMENTS

| 643,544 A | 2/1900 | Simmons |
| 1,838,825 A | 12/1931 | Goldstein |

(Continued)

FOREIGN PATENT DOCUMENTS

DE   893 296   12/1953

(Continued)

OTHER PUBLICATIONS

International Search Report, dated Jan. 19, 2004.

*Primary Examiner*—John Q. Nguyen
*Assistant Examiner*—William E Dondero
(74) *Attorney, Agent, or Firm*—Brinks Hofer Gilson & Lione

(57) ABSTRACT

The invention relates to an apparatus (1) for adjusting the length of an infusion tube (2) comprising a first wall (3) and a second wall (4) and at least one connecting element (5) connecting the first wall (3) to the second wall (4), said connecting element (5) being situated at a distance to the peripheral circumference of the walls (6), and wherein the distance between the walls in radial distance to said connecting element provides an inlet opening extending around the connecting element having a width (M) measured between the walls (3, 4); and wherein the apparatus comprises at least one attachment device (8) for securing the infusion tube (2). Hereby a winding of an infusion tube is enabled for adjusting the connection length between pump and the site of infusion anywhere on the infusion tube and on any kind of infusion tube, said apparatus being independent of the infusion unit. Thus, the apparatus enables reuse due to its independence of the pump. The system also enables the user to position the winding unit on any suitable place in his/her body with regard to physiology and to clothing.

14 Claims, 5 Drawing Sheets

U.S. PATENT DOCUMENTS

| | | |
|---|---|---|
| 1,991,103 A | 2/1935 | King |
| 2,047,010 A | 7/1936 | Dickinson |
| 2,295,849 A | 9/1942 | Kayden |
| 2,319,731 A | 5/1943 | Garrett |
| 2,533,731 A | 12/1950 | Gomberg |
| 2,630,803 A | 3/1953 | Baran |
| 2,690,529 A | 9/1954 | Lindblad |
| 2,730,099 A | 1/1956 | Sullivan |
| 2,839,060 A | 6/1958 | Ormo |
| 2,936,141 A | 5/1960 | Rapata |
| 2,952,420 A | 9/1960 | Von Hoorn |
| 3,055,361 A | 9/1962 | Ballard |
| 3,074,541 A | 1/1963 | Roehr |
| 3,107,785 A | 10/1963 | Roehr |
| 3,154,080 A | 10/1964 | Rowan et al. |
| 3,317,166 A | 5/1967 | Janssen |
| 3,545,286 A | 12/1970 | Stenstrom |
| 3,610,240 A | 10/1971 | Harautuneian |
| 3,648,999 A | 3/1972 | Bauer |
| 3,783,996 A | 1/1974 | Gerard et al. |
| 3,814,097 A | 6/1974 | Ganderton et al. |
| 3,831,729 A | 8/1974 | Howard |
| 3,840,011 A | 10/1974 | Wright |
| 3,865,236 A | 2/1975 | Rycroft |
| 3,942,528 A | 3/1976 | Loeser |
| 3,986,508 A | 10/1976 | Barrington |
| 4,014,328 A | 3/1977 | Cluff et al. |
| 4,022,205 A | 5/1977 | Tenczar |
| 4,082,638 A * | 4/1978 | Jumer .................. 204/213 |
| 4,146,113 A | 3/1979 | Gavel |
| 4,150,798 A | 4/1979 | Aragon |
| 4,188,950 A | 2/1980 | Wardlaw |
| 4,201,406 A | 5/1980 | Dennehey et al. |
| 4,227,528 A | 10/1980 | Wardlaw |
| 4,267,836 A | 5/1981 | Whitney et al. |
| 4,306,705 A | 12/1981 | Svenson |
| 4,315,505 A | 2/1982 | Crandall et al. |
| 4,334,551 A | 6/1982 | Pfister |
| D267,199 S | 12/1982 | Koenig |
| 4,365,630 A | 12/1982 | McFarlane |
| 4,400,861 A | 8/1983 | Parker |
| 4,406,042 A | 9/1983 | McPhee |
| 4,458,344 A | 7/1984 | Coogler |
| 4,472,024 A | 9/1984 | Konomura et al. |
| 4,473,369 A | 9/1984 | Lueders et al. |
| 4,500,312 A | 2/1985 | McFarlane |
| 4,517,971 A | 5/1985 | Sorbonned |
| 4,530,695 A | 7/1985 | Phillips et al. |
| 4,531,686 A | 7/1985 | Shaw |
| 4,576,846 A | 3/1986 | Noel |
| 4,606,735 A | 8/1986 | Wilder et al. |
| 4,610,469 A | 9/1986 | Wolff-Mooij |
| 4,616,790 A | 10/1986 | Beltran |
| 4,619,349 A | 10/1986 | Braun |
| 4,635,683 A | 1/1987 | Nielsen |
| 4,637,404 A | 1/1987 | Gessman |
| 4,662,873 A | 5/1987 | Lash et al. |
| 4,682,702 A | 7/1987 | Gach |
| 4,713,059 A | 12/1987 | Bickelhaupt et al. |
| 4,734,092 A | 3/1988 | Millerd |
| 4,755,173 A | 7/1988 | Konopka et al. |
| 4,758,020 A | 7/1988 | Boyd |
| 4,800,629 A | 1/1989 | Ikeda |
| 4,802,638 A | 2/1989 | Burger et al. |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,878,897 A | 11/1989 | Katzin |
| 4,895,570 A | 1/1990 | Larkin |
| D306,500 S | 3/1990 | Brahler |
| 4,913,369 A | 4/1990 | Lia et al. |
| 4,917,669 A | 4/1990 | Bonaldo |
| 4,935,010 A | 6/1990 | Cox et al. |
| 4,950,163 A | 8/1990 | Zimble |
| 4,950,252 A | 8/1990 | Luther et al. |
| 4,978,338 A | 12/1990 | Melsky et al. |
| 4,982,842 A | 1/1991 | Hollister |
| 4,986,817 A | 1/1991 | Code |
| 4,994,045 A | 2/1991 | Ranford |
| 5,011,475 A | 4/1991 | Olsen |
| 5,024,662 A | 6/1991 | Menes et al. |
| 5,067,496 A | 11/1991 | Eisele |
| 5,077,872 A | 1/1992 | Guthammar |
| 5,083,757 A | 1/1992 | Barsky |
| 5,098,389 A | 3/1992 | Cappucci |
| 5,112,313 A | 5/1992 | Sallee |
| 5,116,319 A | 5/1992 | Van den Haak |
| 5,116,324 A | 5/1992 | Brierley et al. |
| 5,116,325 A | 5/1992 | Paterson |
| 5,121,751 A | 6/1992 | Panalletta |
| 5,134,593 A | 7/1992 | Logan et al. |
| 5,134,594 A | 7/1992 | Woo |
| 5,137,524 A | 8/1992 | Lynn et al. |
| 5,141,496 A | 8/1992 | Dalto et al. |
| 5,147,319 A | 9/1992 | Ishikawa et al. |
| 5,147,375 A | 9/1992 | Sullivan et al. |
| 5,161,681 A | 11/1992 | Kemp et al. |
| 5,163,915 A | 11/1992 | Holleron |
| 5,176,662 A | 1/1993 | Bartholomew et al. |
| 5,188,314 A | 2/1993 | Peters |
| 5,188,611 A | 2/1993 | Orgain |
| RE34,223 E | 4/1993 | Bonaldo |
| 5,222,947 A | 6/1993 | D'Amico |
| 5,232,454 A | 8/1993 | Hollister |
| 5,236,143 A | 8/1993 | Dragon |
| 5,240,199 A | 8/1993 | Peters |
| 5,248,301 A | 9/1993 | Koenig et al. |
| 5,256,152 A | 10/1993 | Marks |
| 5,257,980 A | 11/1993 | Van Antwerp et al. |
| 5,265,822 A * | 11/1993 | Shober et al. ............ 242/388.2 |
| 5,269,799 A | 12/1993 | Daniel |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,343,637 A | 9/1994 | Schindler |
| 5,350,392 A | 9/1994 | Purcell et al. |
| 5,354,280 A | 10/1994 | Haber et al. |
| 5,366,469 A | 11/1994 | Steg et al. |
| 5,372,592 A | 12/1994 | Gambale |
| 5,376,082 A | 12/1994 | Phelps |
| 5,380,067 A | 1/1995 | Turvill et al. |
| 5,384,174 A | 1/1995 | Ward et al. |
| 5,387,197 A | 2/1995 | Smith et al. |
| 5,388,931 A | 2/1995 | Carlson |
| 5,390,669 A | 2/1995 | Stuart et al. |
| 5,391,151 A | 2/1995 | Wilmot |
| 5,403,288 A | 4/1995 | Stanners |
| 5,405,332 A | 4/1995 | Opalek |
| 5,429,607 A | 7/1995 | McPhee |
| 5,429,613 A | 7/1995 | D'Amico |
| 5,433,307 A | 7/1995 | Jeppe |
| D362,718 S | 9/1995 | Deily et al. |
| 5,449,349 A | 9/1995 | Sallee et al. |
| 5,487,506 A | 1/1996 | Drummond et al. |
| 5,490,841 A | 2/1996 | Landis |

| | | | | | | |
|---|---|---|---|---|---|---|
| 5,492,313 | A | 2/1996 | Pan et al. | 6,123,690 | A | 9/2000 | Mejslov |
| 5,505,709 | A | 4/1996 | Funderburk et al. | 6,132,755 | A | 10/2000 | Eicher et al. |
| 5,507,730 | A | 4/1996 | Haber et al. | 6,183,464 | B1 | 2/2001 | Sharp et al. |
| 5,519,167 | A | 5/1996 | Kunimoto et al. | 6,193,694 | B1 | 2/2001 | Bell et al. |
| 5,520,654 | A | 5/1996 | Wahlberg | 6,219,574 | B1 | 4/2001 | Cormier et al. |
| 5,522,803 | A | 6/1996 | Teissen-Simony | 6,221,058 | B1 | 4/2001 | Kao et al. |
| 5,533,974 | A | 7/1996 | Gaba | 6,248,093 | B1 | 6/2001 | Moberg |
| 5,540,709 | A | 7/1996 | Ramel | 6,293,925 | B1 | 9/2001 | Safabash et al. |
| 5,545,143 | A | 8/1996 | Fischell | 6,302,866 | B1 | 10/2001 | Marggi |
| 5,545,152 | A | 8/1996 | Funderburk et al. | 6,319,232 | B1 | 11/2001 | Kashmer |
| 5,554,130 | A | 9/1996 | McDonald et al. | 6,322,535 | B1 | 11/2001 | Hitchins et al. |
| 5,558,650 | A | 9/1996 | McPhee | 6,322,808 | B1 | 11/2001 | Trautman et al. |
| 5,562,636 | A | 10/1996 | Utterberg | 6,334,856 | B1 | 1/2002 | Allen et al. |
| 5,584,813 | A | 12/1996 | Livingston et al. | 6,355,021 | B1 | 3/2002 | Nielsen et al. |
| 5,591,188 | A | 1/1997 | Waisman | 6,379,335 | B1 | 4/2002 | Rigon et al. |
| 5,599,309 | A | 2/1997 | Marshall et al. | D456,692 | S * | 5/2002 | Epstein ............... D8/356 |
| 5,599,315 | A | 2/1997 | McPhee | 6,387,076 | B1 | 5/2002 | Landuyt |
| 5,599,318 | A | 2/1997 | Sweeney et al. | 6,488,663 | B1 | 12/2002 | Steg |
| 5,628,765 | A | 5/1997 | Morita | 6,517,517 | B1 | 2/2003 | Farrugia et al. |
| 5,643,214 | A | 7/1997 | Marshall | 6,520,938 | B1 | 2/2003 | Funderburk et al. |
| 5,643,216 | A | 7/1997 | White | D472,316 | S | 3/2003 | Douglas et al. |
| 5,643,220 | A | 7/1997 | Cosme | D472,630 | S | 4/2003 | Douglas et al. |
| 5,662,617 | A | 9/1997 | Odell et al. | 6,572,586 | B1 | 6/2003 | Wojcik |
| 5,665,071 | A | 9/1997 | Wyrick | 6,579,267 | B2 | 6/2003 | Lynch et al. |
| 5,665,075 | A | 9/1997 | Gyure et al. | 6,582,397 | B2 | 6/2003 | Alesi et al. |
| 5,681,323 | A | 10/1997 | Arick | 6,595,962 | B1 | 7/2003 | Perthu |
| 5,695,476 | A | 12/1997 | Harris | 6,607,509 | B2 | 8/2003 | Bobroff et al. |
| 5,704,920 | A | 1/1998 | Gyure | 6,607,511 | B2 | 8/2003 | Halseth et al. |
| 5,709,516 | A | 1/1998 | Peterson et al. | 6,629,949 | B1 | 10/2003 | Douglas |
| 5,714,225 | A | 2/1998 | Hansen et al. | 6,645,182 | B1 | 11/2003 | Szabo |
| 5,741,288 | A | 4/1998 | Rife | 6,685,674 | B2 | 2/2004 | Douglas et al. |
| 5,752,923 | A | 5/1998 | Terwilliger | 6,702,779 | B2 | 3/2004 | Connelly et al. |
| 5,810,835 | A | 9/1998 | Ryan et al. | 6,726,649 | B2 | 4/2004 | Swenson et al. |
| 5,820,598 | A | 10/1998 | Gazza et al. | 6,736,797 | B1 | 5/2004 | Larsen et al. |
| D402,538 | S | 12/1998 | Wagter et al. | 6,749,589 | B1 | 6/2004 | Douglas et al. |
| 5,843,001 | A | 12/1998 | Goldenberg | 6,790,199 | B1 | 9/2004 | Gianakos |
| 5,851,197 | A | 12/1998 | Marano et al. | 6,805,686 | B1 | 10/2004 | Fathallah et al. |
| 5,858,001 | A | 1/1999 | Tsals et al. | 6,811,545 | B2 | 11/2004 | Vaillancourt |
| 5,865,806 | A | 2/1999 | Howell | 6,814,720 | B2 | 11/2004 | Olsen et al. |
| 5,873,540 | A | 2/1999 | Hardin | 6,824,530 | B2 | 11/2004 | Wagner et al. |
| 5,899,886 | A | 5/1999 | Cosme | 6,824,531 | B1 | 11/2004 | Zecha, Jr. et al. |
| 5,913,846 | A | 6/1999 | Szabo | 6,830,562 | B2 | 12/2004 | Mogensen et al. |
| 5,915,640 | A | 6/1999 | Wagter et al. | 6,837,877 | B2 | 1/2005 | Zurcher |
| 5,919,167 | A | 7/1999 | Mulhauser et al. | 6,840,922 | B2 | 1/2005 | Nielsen et al. |
| 5,925,032 | A | 7/1999 | Clements | 6,880,701 | B2 | 4/2005 | Bergeron et al. |
| 5,947,935 | A | 9/1999 | Rhinehart et al. | 6,916,017 | B2 | 7/2005 | Noe |
| 5,951,523 | A | 9/1999 | Osterlind et al. | 6,923,791 | B2 | 8/2005 | Douglas |
| 5,954,643 | A | 9/1999 | VanAntwerp et al. | 6,926,694 | B2 | 8/2005 | Marano-Ford et al. |
| 5,957,892 | A | 9/1999 | Thorne | 6,939,331 | B2 | 9/2005 | Ohshima |
| 5,968,011 | A | 10/1999 | Larsen et al. | 6,949,084 | B2 | 9/2005 | Marggi et al. |
| 5,975,120 | A | 11/1999 | Novosel | 2001/0004970 | A1 | 6/2001 | Hollister et al. |
| 5,980,488 | A | 11/1999 | Thorne | 2001/0016714 | A1 | 8/2001 | Bell et al. |
| 5,980,506 | A | 11/1999 | Mathiasen | 2001/0021827 | A1 | 9/2001 | Ferguson et al. |
| 5,984,224 | A | 11/1999 | Yang | 2001/0039401 | A1 | 11/2001 | Ferguson et al. |
| 5,984,897 | A | 11/1999 | Peterson et al. | 2001/0041875 | A1 | 11/2001 | Higuchi et al. |
| 5,992,787 | A | 11/1999 | Burke | 2002/0022855 | A1 | 2/2002 | Bobroff et al. |
| D417,733 | S | 12/1999 | Howell et al. | 2002/0068904 | A1 | 6/2002 | Bierman et al. |
| 6,017,328 | A | 1/2000 | Fischell et al. | 2002/0072720 | A1 | 6/2002 | Hague et al. |
| D421,119 | S | 2/2000 | Musgrave et al. | 2002/0077599 | A1 | 6/2002 | Wojcik |
| 6,039,629 | A | 3/2000 | Mitchell | 2002/0107489 | A1 | 8/2002 | Lee |
| 6,042,570 | A | 3/2000 | Bell et al. | 2002/0111581 | A1 | 8/2002 | Sasso |
| 6,045,533 | A | 4/2000 | Kriesel et al. | 2002/0145073 | A1 | 10/2002 | Swanson et al. |
| 6,050,976 | A | 4/2000 | Thorne et al. | 2002/0156424 | A1 | 10/2002 | Suzuki et al. |
| 6,056,718 | A | 5/2000 | Funderburk et al. | 2002/0156427 | A1 | 10/2002 | Suzuki et al. |
| 6,074,371 | A | 6/2000 | Fischell | 2002/0161332 | A1 | 10/2002 | Ramey |
| 6,086,008 | A | 7/2000 | Gray et al. | 2002/0169419 | A1 | 11/2002 | Steg |
| 6,086,575 | A | 7/2000 | Mejslov | 2002/0173748 | A1 | 11/2002 | McConnell et al. |
| 6,090,068 | A | 7/2000 | Chanut | 2002/0183688 | A1 | 12/2002 | Lastovich et al. |
| 6,093,172 | A | 7/2000 | Funderburk et al. | 2002/0189688 | A1 | 12/2002 | Roorda |
| 6,093,179 | A | 7/2000 | O'Hara et al. | 2002/0193737 | A1 | 12/2002 | Popovsky |
| 6,099,503 | A | 8/2000 | Stradella | 2002/0193744 | A1 | 12/2002 | Alesi et al. |
| 6,105,218 | A | 8/2000 | Reekie | 2003/0038209 | A1* | 2/2003 | Remeczky ............... 242/610.6 |
| 6,120,482 | A | 9/2000 | Szabo | 2003/0069548 | A1 | 4/2003 | Connelly et al. |

| | | | | | | |
|---|---|---|---|---|---|---|
| 2003/0105430 A1 | 6/2003 | Lavi et al. | DE | 299 21 406 U1 | | 11/2002 |
| 2003/0109829 A1 | 6/2003 | Mogensen et al. | DK | 37 22 893 C1 | | 6/1988 |
| 2003/0122023 A1* | 7/2003 | Pitcher .................. 242/388.1 | DK | 38 23 447 | | 2/1996 |
| 2003/0125669 A1 | 7/2003 | Safabash et al. | DK | 196 10 692 A1 | | 9/1997 |
| 2003/0125678 A1 | 7/2003 | Swenson et al. | DK | 198 47 143 A1 | | 1/2000 |
| 2003/0130619 A1 | 7/2003 | Safabash et al. | DK | 100 49 001 A1 | | 4/2002 |
| 2003/0139704 A1 | 7/2003 | Lin | EP | 0 188 014 B1 | | 10/1985 |
| 2003/0158520 A1 | 8/2003 | Safabash et al. | EP | 0 239 244 B1 | | 2/1987 |
| 2003/0176843 A1 | 9/2003 | Wilkinson | EP | 0 298 521 B1 | | 9/1990 |
| 2003/0181863 A1 | 9/2003 | Ackley et al. | EP | 0 184 231 B1 | | 1/1992 |
| 2003/0181868 A1 | 9/2003 | Swenson | EP | 0 475 857 | | 3/1992 |
| 2003/0181873 A1 | 9/2003 | Swenson | EP | 0 544 837 B1 | | 6/1993 |
| 2003/0181874 A1 | 9/2003 | Bressler et al. | EP | 0 633 039 | | 7/1994 |
| 2003/0187394 A1 | 10/2003 | Wilkinson et al. | EP | 0 651 662 B1 | | 5/1995 |
| 2003/0187395 A1 | 10/2003 | Gabel et al. | EP | 0 714 631 B1 | | 6/1996 |
| 2003/0199823 A1 | 10/2003 | Bobroff et al. | EP | 744 183 A2 | | 11/1996 |
| 2003/0216686 A1 | 11/2003 | Lynch et al. | EP | 0 747 006 A1 | | 12/1996 |
| 2003/0225373 A1 | 12/2003 | Bobroff et al. | EP | 0 688 232 B1 | | 12/1998 |
| 2003/0225374 A1 | 12/2003 | Mathiasen | EP | 0 884 108 A1 | | 12/1998 |
| 2003/0229308 A1 | 12/2003 | Tsals et al. | EP | 0 931 560 A1 | | 7/1999 |
| 2003/0229316 A1 | 12/2003 | Hwang et al. | EP | 0 956 879 A1 | | 11/1999 |
| 2004/0002682 A1 | 1/2004 | Kovelman et al. | EP | 1 045 145 A1 | | 10/2000 |
| 2004/0006316 A1 | 1/2004 | Patton | EP | 1 086 718 A | | 3/2001 |
| 2004/0026840 A1 | 2/2004 | Eckel et al. | EP | 1 125 593 A1 | | 8/2001 |
| 2004/0044306 A1 | 3/2004 | Lynch et al. | EP | 1 167 765 A2 | | 1/2002 |
| 2004/0049159 A1 | 3/2004 | Barrus et al. | EP | 0 894 216 B1 | | 7/2003 |
| 2004/0068231 A1 | 4/2004 | Blondeau | EP | 1 380 315 A1 | | 1/2004 |
| 2004/0087913 A1 | 5/2004 | Rogers et al. | FR | 576 849 | | 8/1924 |
| 2004/0111068 A1 | 6/2004 | Swenson | FR | 2 611 013 | | 8/1988 |
| 2004/0112781 A1 | 6/2004 | Hofverberg et al. | FR | 2725902 | | 10/1994 |
| 2004/0116865 A1 | 6/2004 | Bengtsson | FR | 2 733 915 | | 11/1996 |
| 2004/0138612 A1 | 7/2004 | Shermer et al. | FR | 2 781 617 A1 | | 1/2000 |
| 2004/0138620 A1 | 7/2004 | Douglas et al. | GB | 591730 | | 3/1946 |
| 2004/0143216 A1 | 7/2004 | Douglas et al. | GB | 906574 | | 9/1962 |
| 2004/0143218 A1 | 7/2004 | Das | GB | 1 268 575 | | 3/1972 |
| 2004/0158202 A1 | 8/2004 | Jensen | GB | 1 403 034 | | 8/1975 |
| 2004/0158207 A1 | 8/2004 | Hunn et al. | GB | 2 224 808 A | | 5/1990 |
| 2004/0159736 A1* | 8/2004 | Cook ..................... 242/388.1 | GB | 2 270 552 A | | 3/1994 |
| 2004/0162518 A1 | 8/2004 | Connelly et al. | JP | 5326062 A | | 12/1993 |
| 2004/0171989 A1 | 9/2004 | Horner et al. | JP | 05326062 A | | 12/1993 |
| 2004/0178098 A1 | 9/2004 | Swenson et al. | JP | 3140740 | | 2/2000 |
| 2004/0186446 A1 | 9/2004 | Ohshima | JP | 2000059877 A | | 2/2000 |
| 2004/0199123 A1 | 10/2004 | Nielsen | JP | 2002-028246 | | 1/2002 |
| 2004/0204687 A1 | 10/2004 | Mogensen et al. | NL | 1017427 C | | 11/2002 |
| 2004/0204690 A1 | 10/2004 | Yashiro et al. | WO | WO 87/06474 | | 11/1987 |
| 2004/0220528 A1 | 11/2004 | Garcia, Jr. | WO | WO 93/05840 | | 4/1993 |
| 2004/0238392 A1 | 12/2004 | Peterson et al. | WO | WO 94/20160 | | 9/1994 |
| 2004/0243065 A1 | 12/2004 | McConnell et al. | WO | WO 95/28327 A | | 10/1995 |
| 2004/0254433 A1 | 12/2004 | Bandis et al. | WO | WO 96/35472 | | 11/1996 |
| 2004/0260235 A1 | 12/2004 | Douglas | WO | WO 98/09065 | | 3/1998 |
| 2004/0260250 A1 | 12/2004 | Harris et al. | WO | WO 98/58693 | | 12/1998 |
| 2005/0035014 A1 | 2/2005 | Cane | WO | WO 99/07435 | | 2/1999 |
| 2005/0101932 A1 | 5/2005 | Cote et al. | WO | WO 99/33504 | | 7/1999 |
| 2005/0101933 A1 | 5/2005 | Marrs et al. | WO | WO 99/61815 | | 12/1999 |
| 2005/0107743 A1 | 5/2005 | Fangrow, Jr. | WO | WO 00/02614 | | 1/2000 |
| 2005/0113761 A1 | 5/2005 | Faust et al. | WO | WO 00/03757 | | 1/2000 |
| 2005/0119637 A1 | 6/2005 | Lundgren et al. | WO | WO 00/44324 A1 | | 8/2000 |
| 2005/0124936 A1 | 6/2005 | Mogensen et al. | WO | WO 01/04507 A1 | | 1/2001 |
| 2005/0159709 A1 | 7/2005 | Wilkinson | WO | WO 01/30419 A2 | | 5/2001 |
| 2005/0215979 A1 | 9/2005 | Konerup et al. | WO | WO 01/68180 | | 9/2001 |
| 2005/0251098 A1 | 11/2005 | Wyss et al. | WO | WO 01/81785 A1 | | 11/2001 |
| 2005/0277892 A1 | 12/2005 | Chen | WO | WO 01/93926 A2 | | 12/2001 |
| 2005/0283114 A1 | 12/2005 | Bresina et al. | WO | WO 02/066854 A1 | | 8/2002 |
| 2006/0030815 A1 | 2/2006 | Csincsura et al. | WO | WO 02/068014 | | 9/2002 |
| | | | WO | WO 02/094352 | | 11/2002 |
| | FOREIGN PATENT DOCUMENTS | | WO | WO 02/100457 | | 12/2002 |
| DE | 1 053 541 | 3/1959 | WO | WO 03/015860 A1 | | 2/2003 |
| DE | DT 26 20 009 A1 | 12/1977 | WO | WO 03/026728 | | 4/2003 |
| DE | 28 03 509 | 8/1979 | WO | WO 2004/030726 A | | 4/2004 |
| DE | 196 31 921 | 3/1997 | WO | WO 2004/087240 | | 10/2004 |
| DE | 298 18 311 U1 | 11/1999 | WO | WO 2005/004973 | | 1/2005 |
| DE | 101 06 074 A1 | 9/2000 | * cited by examiner | | | |

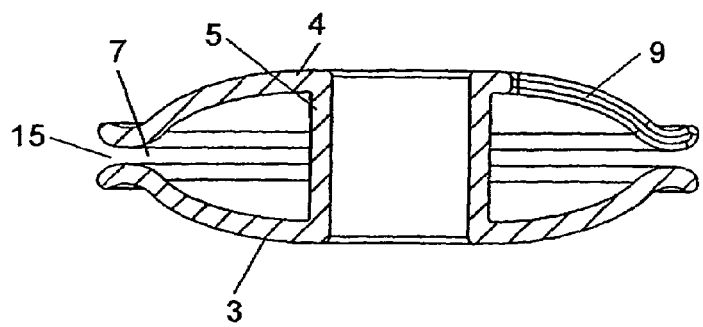
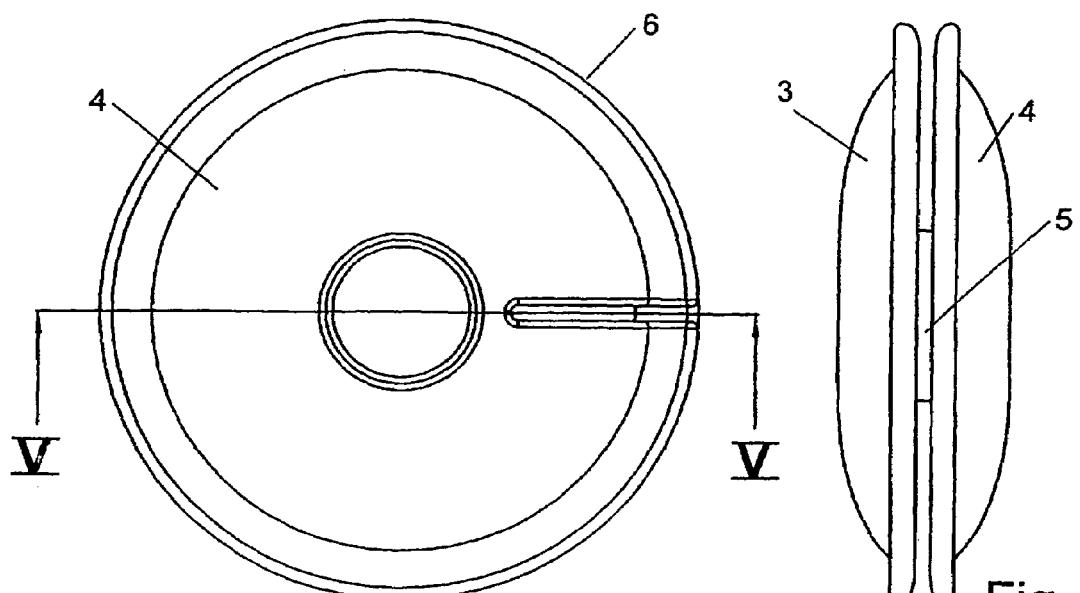
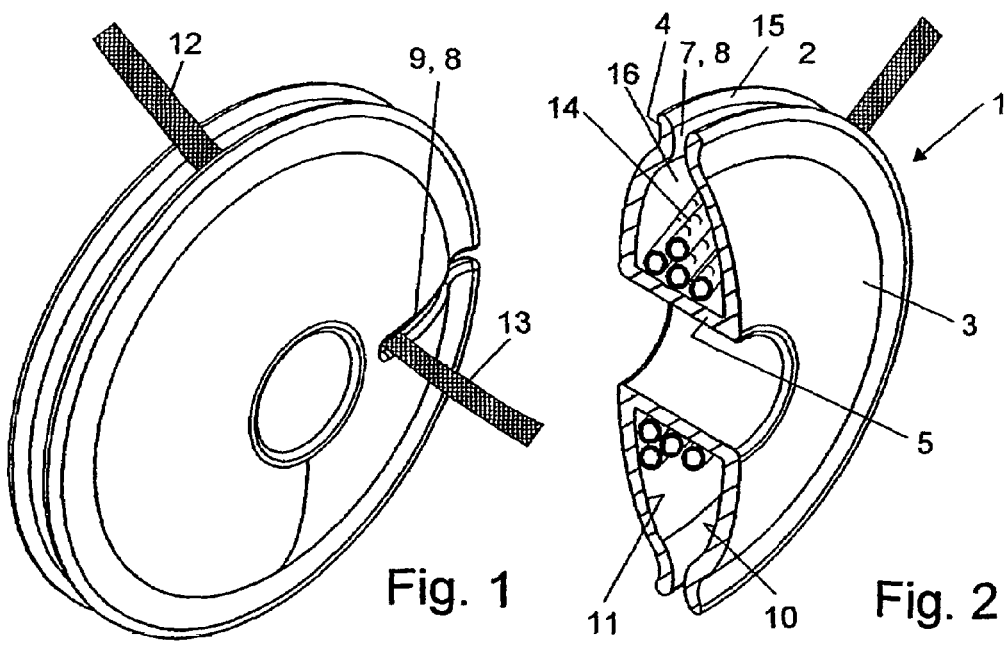

APPARATUS FOR AND A METHOD OF ADJUSTING THE LENGTH OF AN INFUSION TUBE

This application is a continuation of International Application No. PCT/DK2003/000571, filed Sep. 2, 2003, which is a continuation-in-part of U.S. application Ser. No. 10/409,898, filed Apr. 8, 2003 now abandoned, which is a continuation of Danish Application No. PA 2002 01287, filed Sep. 2, 2002, these references are incorporated herein in their entirety.

The invention relates to an apparatus for adjusting the length of an infusion tube comprising a first wall and a second wall and at least one connecting element connecting the first wall to the second wall. The invention also relates to a method of adjusting the length of an infusion tube, said apparatus comprising an apparatus with a first wall and a second wall, between which walls parts of the infusion tube are situated, and further at least one connecting element connecting the first and the second walls to each other.

Use of an infusion kit in combination with an insulin pump necessitates use of a tubular member of a given length, since the distance between the insulin pump and the cannula housing will vary. This variation in the distance between pump and cannula occurs e.g. at night when the pump is sitting on the bedside table. Here the tube may have to be used in its full length. When, during the day, the pump is sitting in the belt of the diabetic, the requisite length of the tube will be smaller—but still variable as the cannula can be located in various places on the body.

Therefore the problem occurs of excessive tubing which may be difficult for the user to position/conceal. That is, when the cannula housing is located in immediate proximity of the pump and the user simultaneously uses a long tube of 110 cm, a worst case scenario will be one in which there will be about 90 cm that are not "in use".

It is desired to develop a winding device that is able to compensate for the above-described problem.

The winding device according to the present invention is typically located in close proximity to the skin—underneath the clothes. Optionally by means of a clip to the trouser waistband.

The winding device must not in any way cause failure of the insulin supply, neither by damage/deformation of tube nor for any other reason.

WO 96/35472 teaches an apparatus of the kind described above, wherein a portable medical pump is described in which a winding unit for the infusion tube is integrally provided. It is the drawback of this system that, apart from the tube constituting an integral part of the pump device, the winding device is constituted of an essentially closed unit, and wherein the winding takes place by rotation of a rotatable sidewall. Such system is mechanically complex and restricts the winding to taking place in proximity of the infusion part and not anywhere on the tube and not on any kind of tube, as the winding system is designed exclusively for the pump it is an integral part of. Furthermore, there is a risk of damaging the tube during the winding due to the essentially closed housing. To the user, the system is not particularly flexible as it is not possible to locate the pump unit to itself and the winding unit to itself. Therefore the unit will be very visible to the user when he/she carries the pump unit.

U.S. Pat. No. 5,265,822 teaches a spool shaped apparatus for adjusting the length of an intravenous supply tube comprising to parallel walls, equipped with slots for removably fixing the supply tube to the spool at a desired length. The spool is oval to better fit into the hand of a patient, who is supposed to carry the apparatus during use. Since infusion processes can be of considerable duration this apparatus has the serious drawback that the patient has to carry it, causing fatigue to the patient.

It is thus an object of the invention to provide an infusion tube adjusting apparatus that can be attached easily to the patient, and by the patient, allowing the patient the freedom of using his/her hands.

It is a further object of the present invention to provide an apparatus and a method that overcome the above drawbacks, and whereby it is possible to perform a winding of an infusion tube to adjust the connecting length between pump and infusion site essentially anywhere on the infusion tube and on any infusion tube, the apparatus being independent of infusion cannula and pump. Thus, the apparatus enables reuse due to the independence of the pump. The system also enables the user to locate the winding unit anywhere on the body suitable to his/her physiology and clothing. It is thus possible to locate it underneath the blouse, in the trouser waistband, pocket or the like when the unit is provided with a clip device. It is also possible to locate the unit directly on the pump by means of attachment means. Finally it is possible to make unit and pump as an integral unit.

This object is obtained by an apparatus of the kind described above and wherein the connecting element is situated at a distance to the peripheral circumference of the walls, and wherein the distance between the walls in radial distance to said connecting element provides an inlet opening extending around the connecting element with a width measured between the walls, and wherein the apparatus comprises at least one attachment device for securing the infusion tube, and wherein the apparatus comprises a further attachment device integrated with the first or second wall, for mounting the apparatus on a carrier face.

The integrated attachment device is preferably resiliently connected to the wall of the infusion tube adjusting apparatus, and converging on the wall. In this way the integrated attachment device can squeeze around the edge of a carrier face such as a belt or a pocket or a fold on an article of clothing.

Hence, the patient—or a helper—can easily attach the apparatus to the patients clothes, ensuring that he/she does not have to carry the apparatus for long periods of time. The attachment device being integrated with the wall ensures that the attachment device is always ready, and at hand when attachment of the apparatus is required or wanted, as compared to strips of tape, safety pens or other loose, non-integrated attachment devices. It also ensured that the patient can perform the operation of attaching and detaching the apparatus with a single hand, and without pulling the tubing, thereby preventing causing pain to the patient at the insertion site of the needle, which is attached to the infusion tubing. Further, the integrated attachment device can easily be detached from the patients clothes, when this is required or wanted.

When the apparatus is attached to the patients clothes or belt of the patient, using the integrated attachment device, his/her hands are free for other uses. This is particularly beneficial when the length of the tube has to be adjusted.

However, the integrated attachment device due to the resilient connection to the wall of the tube adjusting apparatus will also provide a firm grip on the carrier surface allowing the option of performing the operation of adjusting the tube length using a single hand only.

The integrated attachment device further provides an excellent grip on the apparatus, when the patient wants to carry the apparatus by hand. It is particularly important that the apparatus does not slip, since the end of the tube is connected to a needle at the infusion site. Unintentional jerks on the tube will eventually cause pain to the patient. This aspect is also important when the tube length is adjusted. The adjusting apparatus needs to be firmly secured to the patient while adjusting the length to avoid pain at the injection site.

The object is further obtained by the method described above, and wherein, between the first and the second walls, an inlet opening is provided, between which the tube is pressed such that a first portion and a second portion of the tube is caused to be situated outside the apparatus, and a third portion is delimited by the walls; wherein the entire or portions of the second portion of the tube is wound around the connecting element, said connecting element being situated at a distance to the peripheral circumference of the walls; and wherein the first and seconds portion of the tubes are secured by attachment means.

The apparatus or tube winder, as it may be designated, thus operates in that an infusion tube is introduced between the outer periphery of the first and the second walls and between the lips thereof that provide an inlet opening throughout the entire periphery thereof. Preferably the walls will be cylindrical and this means that it is a kind of drum; and wherein the connecting element between the walls is constituted of a shaft around which the tube can be wound.

Owing to the attachment taking place of the tube when pressed into the attachment device, it is ensured that the tube does not unwind by itself. Now a winding around the connecting element takes place, which element is, as mentioned, comparable with a shaft, and it continues until the tube has reached the desired length.

The second tube portion which is now situated freely will be conveyed into the attachment device and secure that the second tube portion does not unwind. The attachment device is provided primarily by means of a slot in the one wall and extends from the periphery thereof and radially towards the centre. Both the first and the second tube portions can be secured in this slot. However, the apparatus may comprise several slots and located in both walls.

It is a further option that the inlet opening serves as attachment device, the first as well as the second tube portions, located freely outside the unit, being fastened in place by the inlet opening of the peripheral circumference, since it is provided to be so narrow that it squeezes around the tube. The width of the inlet opening is thus selected as a function of the infusion tube used, since this width is slightly smaller than the outer diameter of the infusion tube.

However, the dimensions of infusion tubes being standardised, use of only a few apparatuses will suffice. In this context, the width of the inlet opening is measured by taking the perpendicular distance between the adjoining walls and on the narrowest spot.

Finally, it is possible to combine slot and inlet opening as securing means for the tube ends.

By providing an apparatus according to the invention and further having the first and the second walls that are identically configured bodies arranged in parallel and opposite to each other, a convenient manner of securing the tubing is obtained, such that they do not wind during the other winding of the tube; and also that the tubes do not unwind by themselves again.

By providing an apparatus according to the invention and and further having the connecting element including a cylindrical unit, wherein the longitudinal axis of the cylindrical unit is located perpendicular to the inner faces of the first and second walls, a convenient securing is obtained, since the portion of the tube which is not desired to be wound on the connecting element is secured in the slot as such, following which the winding takes place with the remaining part of the tube and subsequently a securing of the slot takes place in the slot of the second tube portion.

By providing an apparatus according to the invention and further having at least a portion of the apparatus manufactured for an elastic material, a convenient embodiment of the apparatus is obtained, which can be likened to a yoyo. The first and the second walls can be e.g. circular, elliptic or rectangular sheet elements.

However, the unit can also be manufactured in two pieces, such that the one wall with the drum part, a female part, being cast in one operation, and the second wall with a second drum part, a male part fitting by force fit into the first portion, being manufactured in a second moulding process. The two elements are assembled by a click device, the male part comprising an annular bead that is clicked into an annular recess extending on the female part. Furthermore, the apparatus may comprise a clip that can be cast integrally with one of the walls.

The invention will now be explained in further detail with reference to the drawing, wherein:

FIG. 1 is an exemplary embodiment of the invention, seen in a perspective view;

FIG. 2 is a sectional view of the exemplary embodiment shown in FIG. 1, illustrating an apparatus/a tube winder;

FIG. 3 shows the apparatus shown in FIG. 1, seen from the side;

FIG. 4 shows the apparatus shown in FIG. 1, seen from the front;

FIG. 5 is a sectional view along the line V-V in FIG. 3;

Figure 6A:
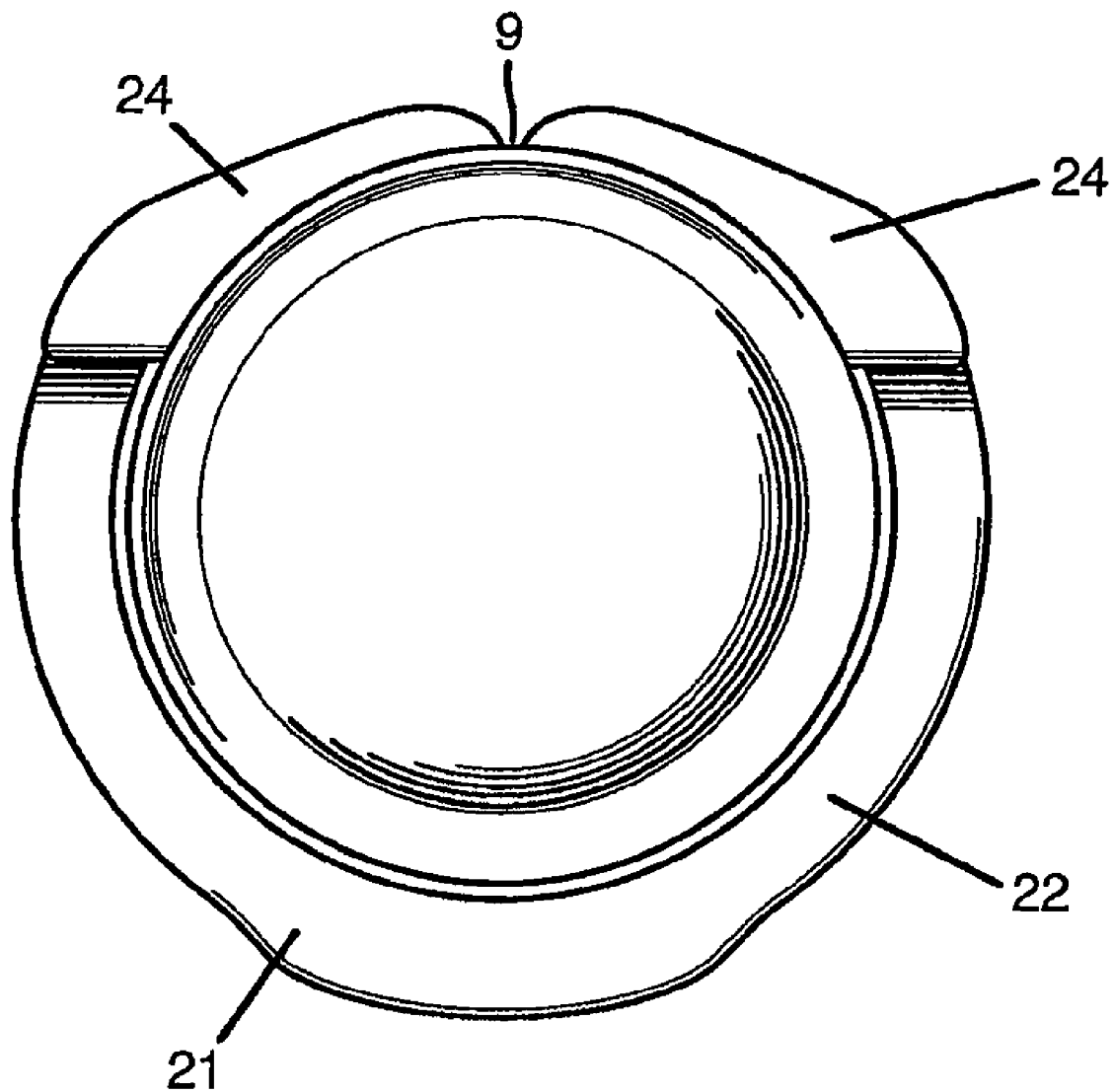
Figure 6B:
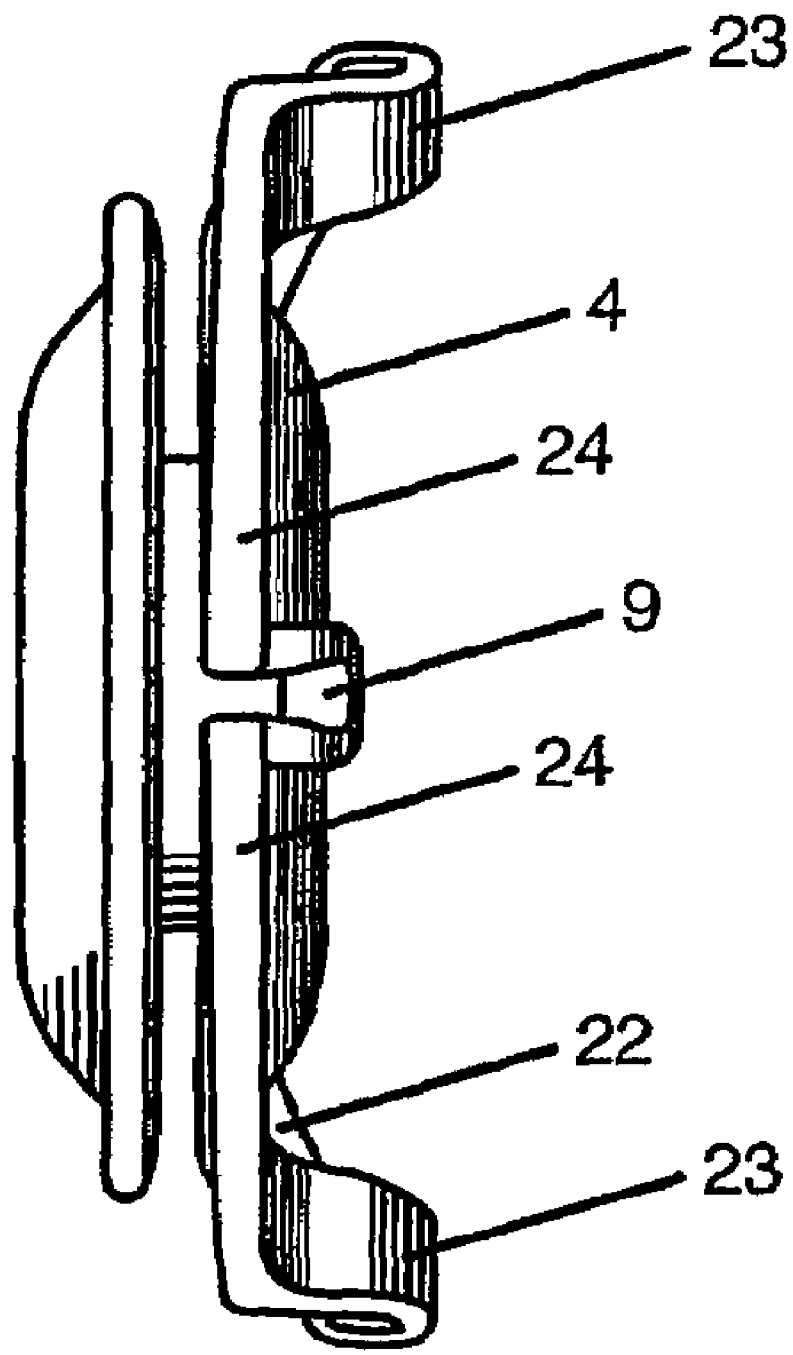
Figure 6C:
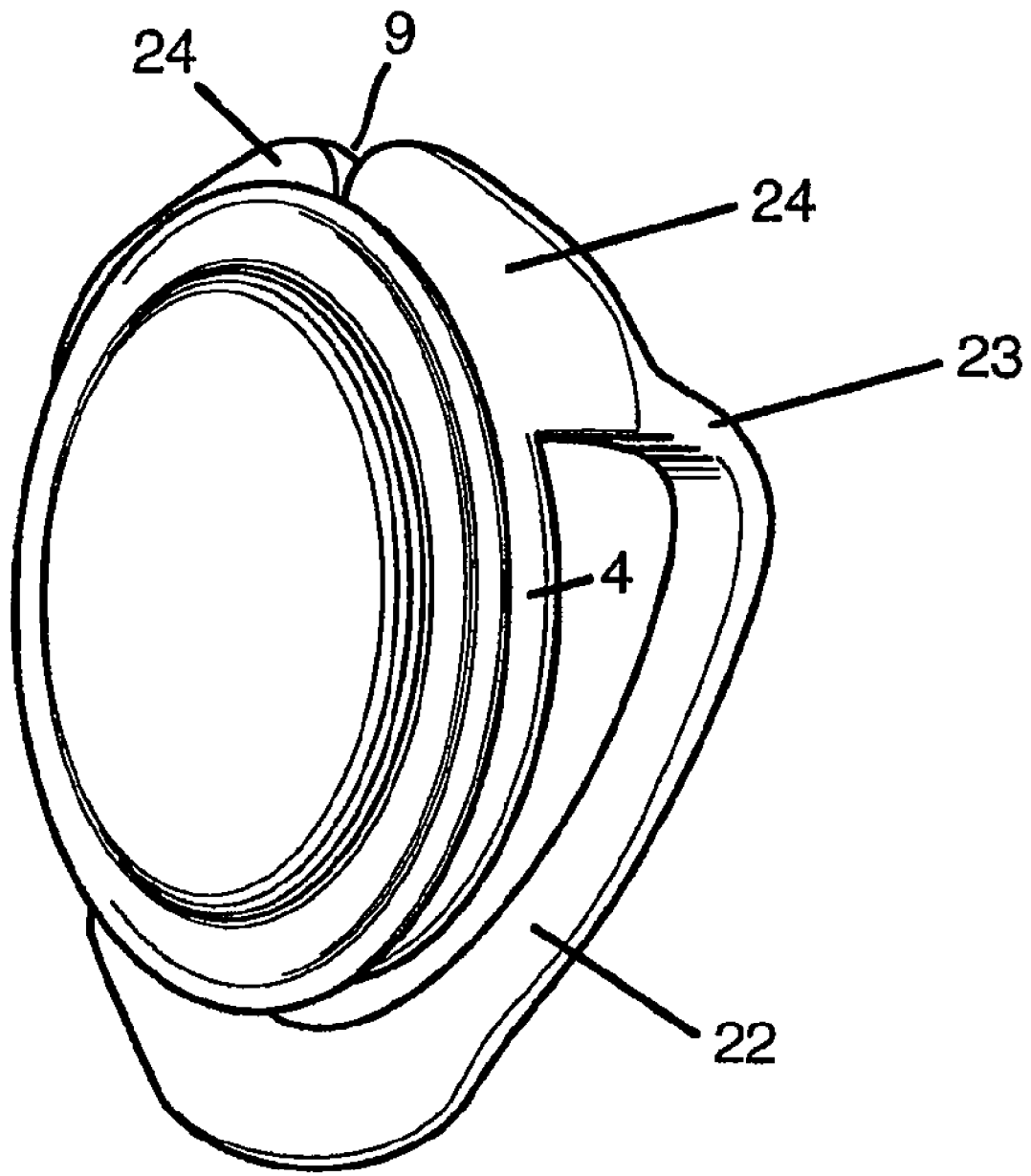
Figure 7:
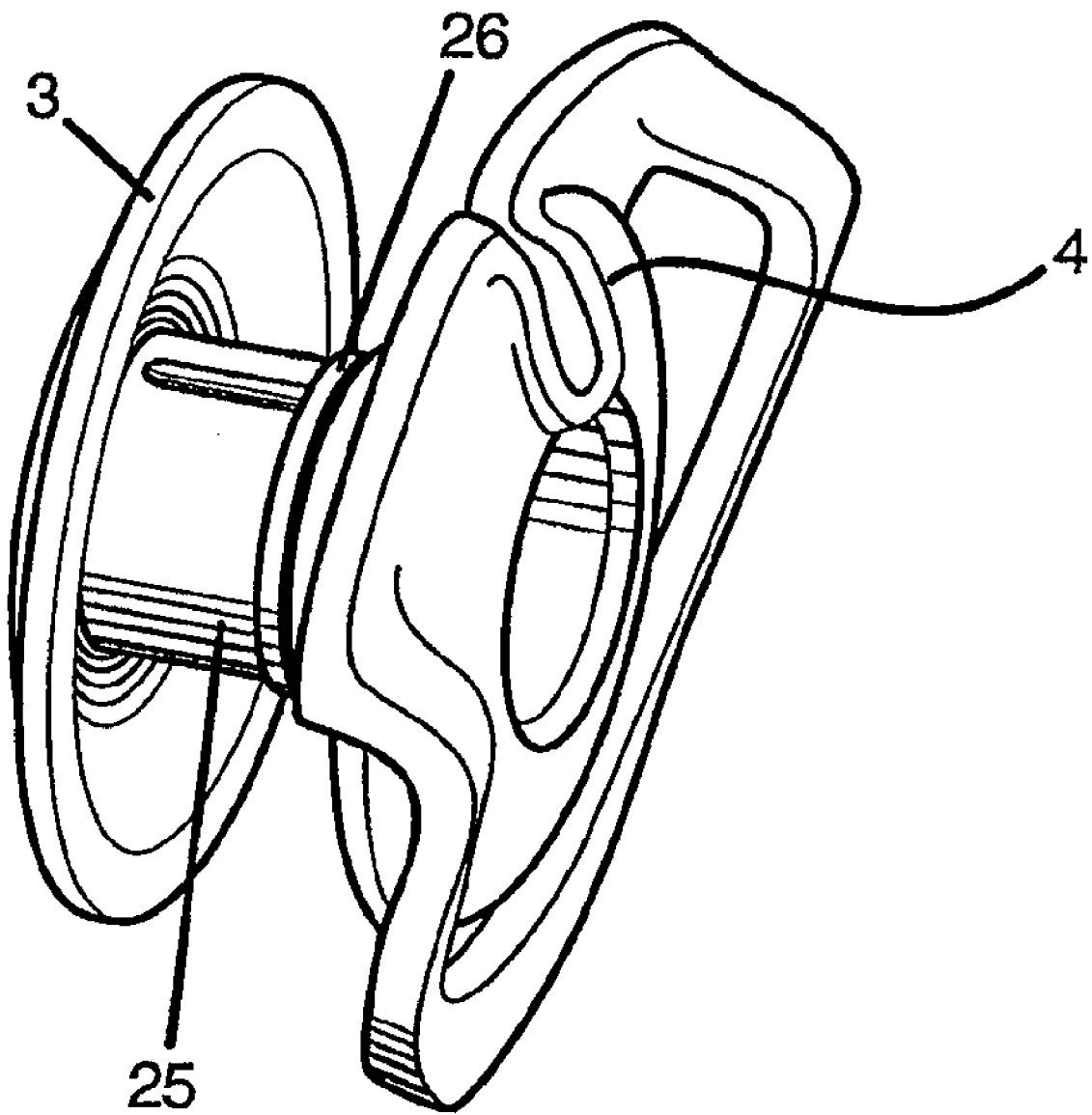

FIGS. 6A-C show an alternative exemplary embodiment of the invention, seen in a perspective view;

FIG. 7 shows the assembling of an apparatus as shown in FIGS. 6A-C.

With reference to FIGS. 1 and 2 the invention will now be explained in further detail, FIG. 1 showing a perspective view of an apparatus 1, and FIG. 2 showing a sectional view of the view of FIG. 1. The apparatus 1 comprises two walls, a first wall 3 and a second wall 4, said walls being provided to be parallel opposite each other; and in the example shown configured to be cylindrical for providing a kind of drum/yoyo; and wherein the two walls 3 and 4 are connected by means of a connecting element 5 configured as a shaft, the central axis of which coincides with the centre of the first and the second walls and extending perpendicular to the faces. At a distance to the connecting element 5, which is thus configured as a cylindrical shaft, the first and the second walls form an inlet opening 7; and wherein the distance between the wall for providing said inlet opening 7 corresponds to the outer diameter of an infusion tube 2 or somewhat smaller as this inlet opening may serve the purpose of squeezing around the tube, such that an unwinding is avoided.

The walls 3 and 4 and the inner faces of the connecting element 5 provide a cavity in which the wound-up infusion tube is situated. The cavity 16 is, in cross section, configured as a funnel with the largest basis corresponding to that face of the connecting element 5 that faces towards the cavity and on the sides delimited by the inner faces of the first and the second wall 3 and 4 that converge towards the inlet opening.

Radially to the inlet opening an inlet area 15 is provided that is also funnel-shaped, but has diverging walls away from the inlet opening 7 and outwards, since it is the object of this funnel to assist in the catching of the tube during winding. The first and the second walls are cylindrical and in this case have the shape of curved shells.

The apparatus is conveniently manufactured in an injection moulding process, wherein a thermoplastic elastomer, TPE, or a copolymer, eg a PP copolymer, is preferred; since it is convenient that that the inlet opening 7 has a resilient and elastic abutment on the tube, thereby optionally securing the same without an ensuing risk, however, of exposing the tube to damage.

The one wall, optionally both walls 3, 4, has/have a slot 9 extending radially from the peripheral circumference 6 of the wall and towards the centre, said slot serving the purpose of constituting a starting point on the tube prior to winding, as the tube is squeezed in place in said slot. The length of the slot is adapted such that its bottom is located at a smaller distance from the surface of the connecting element 5. The slot also serves as securing means for the tube portion when it is wound. The delimiting side faces of the slot conveniently diverge towards the centre.

The winding process will be explained below.

The slot 9 thus has a width corresponding essentially to the width of the inlet opening 7 and is approximately 1.4 mm; being, however, slightly less. Both the slot 9 and the inlet opening 7 serve as attachment devices 8, as the winding takes place as follows:

The infusion tube 2 to be wound on the apparatus is pressed in through the inlet opening 7 via the inlet area 15 wherein, as mentioned, the funnel-shaped, reversed tunnel of the inlet area 15 ensures that the tube is readily caught.

The first portion of the tube 12 is secured in the slot, subsidiarily with the inlet opening as such, while the second portion of the tube 13 is introduced into the slot 9, such that a securing point is obtained when the winding is at an end. Between the first and the second tube portions, there is a third portion 14, which is delimited by the walls 3, 4. A winding of the tube takes place by the tube being seized and subsequently wound the number of times required for the infusion tube to acquire the desired length.

The tube will not be wound further when the desired length is acquired, since the securing means or attachment devices 8 have a securing/squeezing function on the tube.

FIG. 1 shows the case in which the securing takes place both in the inlet opening and in the slot. However, it is a very preferred embodiment in those cases where both the first tube portion 12 and the second tube portion 13 are both secured in the slot, and where the starting point will thus be that the first tube portion 12 is located in the slot; that a winding of the tube subsequently takes pace on the drum; and that—when the desired tube length is thus desired, the second tube portion is pressed down into the slot. Of course, it is a consequence of this that, when the first tube portion 12 points in one direction, the second tube portion 13 will point in the opposite direction.

FIGS. 6A-C show an exemplary embodiment in which the product as such is essentially like that of the view shown in FIGS. 1-5, but wherein an attachment device 21 in the shape of a clip is mounted. The clip 21 consists of a partially circular clamp 22 that is located offset perpendicular on the wall 4 on which it is secured, and such that there is a space between the wall and the clamp 22. The clamp 22 is elastically connected to the wall by two bent plate parts 23 that are yet again connected to two constituent parts 24 that are integral with the wall 4. The clamp 22 is attached to the wall 4 in which the slot 9 is situated and such that the two plate parts 24 are arranged symmetrically around said slot, and likewise the elastic clamp 22 is arranged symmetrically around the slot 9. Preferably the clamp part 22 and the wall 4 to which it is attached will have a converging course towards each other as far as that part of the clamp is concerned that is located opposite the two plate parts.

Other embodiments of the attachment device 21 can be applied. E.g. the clip 21 can take the form of a common clothes peg, the elasticity or squeezing urge being provided by a spring. The clip could also be in the shape of a triangular paper clip.

FIG. 7 shows an example of how the product can be manufactured in two parts such that a first wall 3 and a second wall 4 are provided; and wherein each of these walls has a cylindrical element mounted thereon, the centre axis of which coincides with the centre axis of the wall and such that the cylinder 25 of the one wall constitutes a female part, while the cylinder portion 26 of the second wall constitutes a male part. In the delimiting edge of the male part an annular bead is provided which will, when male and female parts are pressed completely against each other, have an engagement in a corresponding annular recess on the inner face of the female part.

The apparatus is used in particular for shortening the length of infusion tubes, wherein the one end of the infusion tube is connected to a pump for infusion of a medicament; and the free end is connected to e.g. a cannula or the like for infusion of a given medicament into a patient. Thus, the pump can be located anywhere on the body, where it may be convenient, and likewise the apparatus can be located anywhere on the body and independently of the position of the infusion pump. The apparatus can be attached to the belt, to the infusion pump as such, on the patient's body or on pieces of clothes if so desired by the user. The apparatus is very flexible and user-friendly and provides the user with ample opportunities for performing the requisite adjustment of the tube length. Usually the tubes have a length of 60-110 cm, as it is essential to the patient to be able to have e.g. a long connection to the pump while asleep, while it is essential to have a short connection to the pump when the patient moves around, the pump being in that case typically positioned on the body.

Thus, the invention enables adjustment of the length, such that the patient can adapt the length as a function of the physical framework. Typically, this is necessary in those cases where insulin pumps are concerned, since such pumps are located at all times on the patient. The winder can be located on clothes rims, belts, etc., by means of the clip device on the winder. Alternatively, By means of e.g. double-adhesive tape, however, the apparatus/tube winder can be located directly on the insulin pump.

The invention claimed is:

1. An apparatus for adjustment of the length of an infusion tube comprising:
   an infusion tube;
   a first wall;
   a second wall;
   at least one connecting element connecting said first wall to said second wall, said connecting element being secured at a distance to a peripheral circumference of the walls; and
   an inlet opening extending around the connecting element, said opening being provided by a distance between said walls in a radial distance from said connecting element, inner faces of the first and the second walls converge from the connecting element towards the inlet opening, said opening having a width (M) measured between the walls, the width M sized to correspond to said diameter of said infusion tube or slightly smaller to allow passage of a single infusion tube through the inlet opening to allow uninterrupted fluid flow through the infusion tube; and at least one elongate slot arranged in at least one of said walls such that said infusion tube can pass through said wall, the slot sized to have a width which is greater than or equal to a diameter of the infusion tube, said at least one slot extending from a periphery of the wall radially towards a center of the wall to substantially said connecting element.

2. An apparatus according to claim 1, wherein the first and the second walls are identically configured bodies arranged in parallel and opposite to each other.

3. An apparatus according to claim 1, wherein the connecting element comprises a cylindrical unit, the longitudinal axis of which is located perpendicular to the inner faces of the first and the second walls.

4. An apparatus according to claim 1, wherein the walls are, at least in the area delimiting the inlet opening, manufactured from an elastic material.

5. An apparatus according to claim 1, wherein the entire apparatus is manufactured from an elastic material.

6. An apparatus according to claim 1, further comprising an attachment device integrated with the first or second wall, for mounting the apparatus on a carrier face.

7. An apparatus according to claim 6, wherein the attachment device is a clip device for mounting of the apparatus on a carrier face.

8. An apparatus according to claim 6, wherein the at least one slot is formed in the wall on which the attachment device for mounting the apparatus on a carrier face is arranged.

9. The apparatus of claim 1, wherein the inlet opening is funnel-shaped, such that the walls diverge away from the inlet opening toward the connecting element.

10. The apparatus of claim 1, wherein the length of the slot is at least twice the diameter of the infusion tube.

11. A method of adjusting the length of an infusion tube using an apparatus according to claim 1, the method comprising:
    inserting the tube through an inlet opening, such that a first portion and a second portion of the tube are positioned outside the apparatus and a third portion is positioned between the walls;
    winding at least a portion of the second portion of the tube around a connecting element; and
    securing first and second end portions of the tube in at least one slot or the inlet opening.

12. A method according to claim 11, further comprising securing the first portion of the tube in the at least one slot, the at least one slot extending from the peripheral circumference of the one wall and towards the center of the wall.

13. A method according to claim 11, further comprising securing a free tube portion at the delimitation of the inlet opening provided at the walls.

14. A method according to claim 11, further comprising securing the second tube portion in the at least one slot, the at least one slot extending from the one peripheral circumference of the one wall and towards the internal area of the wall.

* * * * *

UNITED STATES PATENT AND TRADEMARK OFFICE
CERTIFICATE OF CORRECTION

PATENT NO. : 7,654,484 B2
APPLICATION NO. : 10/526253
DATED : February 2, 2010
INVENTOR(S) : Mogensen et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 729 days.

Signed and Sealed this

Twenty-third Day of November, 2010

David J. Kappos
*Director of the United States Patent and Trademark Office*